United States Patent [19]

van der Baan et al.

[11] Patent Number: 5,118,855
[45] Date of Patent: Jun. 2, 1992

[54] PHOSPHINE COMPOUNDS

[75] Inventors: Julianus L. van der Baan; Friedrich Bickelhaupt; Joachim W. F. K. Barnick, all of Amsterdam, Netherlands

[73] Assignee: Shell Oil Company, Houston, Tex.

[21] Appl. No.: 659,813

[22] Filed: Feb. 25, 1991

[30] Foreign Application Priority Data

Mar. 23, 1990 [GB] United Kingdom ............... 9006576

[51] Int. Cl.$^5$ .................................................. C07F 9/02
[52] U.S. Cl. ............................................................ 568/13
[58] Field of Search ................................................ 568/13

[56] References Cited

U.S. PATENT DOCUMENTS

| 2,999,882 | 9/1961 | Buckler et al. | 568/13 |
| 3,660,495 | 5/1972 | Lin | 568/13 |
| 3,694,412 | 9/1972 | Nozaki | 260/63 |
| 4,818,810 | 4/1989 | Drent | 528/392 |
| 4,835,250 | 5/1989 | Drent | 528/392 |
| 4,843,144 | 6/1989 | Van Broekhoven et al. | 528/392 |
| 4,868,282 | 9/1989 | Van Broekhoven et al. | 528/392 |
| 4,880,903 | 11/1989 | Van Broekhoven et al. | 528/392 |

FOREIGN PATENT DOCUMENTS

| 121965 | 10/1984 | European Pat. Off. |  |
| 181014 | 5/1986 | European Pat. Off. |  |
| 213671 | 3/1987 | European Pat. Off. |  |
| 257663 | 5/1987 | European Pat. Off. |  |
| 311352 | 4/1988 | European Pat. Off. |  |
| 1498773 | 8/1989 | U.S.S.R. | 568/13 |
| 1341857 | 12/1971 | United Kingdom . |  |

OTHER PUBLICATIONS

Complexes of Binucleating Ligands, by R. Kelson and R. Robson, J. Coord. Chem. Feb. 1979, vol. 6, pp. 235-244.

Advanced Materials, Angewandte Chemie, by Henri Brunner and Adolf Sicheneder, vol. 100, No. 5, May 1988.

*Primary Examiner*—Paul F. Shaver

[57] ABSTRACT

Novel 2-($\omega$-hydroxyalkyl)-1,3-bis(diarylphosphino)propane compounds are useful in the production of immobilized bidentate phosphine ligands for catalyst production.

11 Claims, No Drawings

PHOSPHINE COMPOUNDS

FIELD OF THE INVENTION

This invention relates to certain novel compounds of phosphorus. More particularly, the invention relates to certain hydroxyalkyl-substituted bidentate ligands of phosphorus useful in the production of polymerization catalysts.

BACKGROUND OF THE INVENTION

The class of linear alternating polymers of carbon monoxide and at least one ethylenically unsaturated hydrocarbon are known in the art. An early disclosure of the production of such materials was by Nozaki, U.S. Pat. No. 3,694,412, who employed monodentate aromatic phosphine complexes of palladium moieties and certain inert solvents. More recent processes for the production of such polymers are disclosed by a number of published European Patent Applications including 121,965, 181,014, 213,671 and 257,663. These polymers, now known as polyketones or polyketone polymers, are represented by the repeating formula

—CO—A— wherein A represents a moiety of at least one ethylenically unsaturated hydrocarbon polymerized through the ethylenic unsaturation thereof. The scope of the polymerization process illustrated by the above European Patent Applications is extensive but, without wishing to be limited, a preferred catalyst composition is formed from a compound of palladium, an anion of a strong non-hydrohalogenic acid and a bidentate ligand of phosphorus. These catalysts are typically homogeneous catalysts, i.e., the catalysts are soluble in the reaction media, and are used in quantities which are relatively small relative to the reactants.

Recovery of the catalyst from the reaction media is desirable for a number of reasons including the economic advantages obtained by being able to reuse the catalyst components and also from a product purity standpoint.

One method proposed for providing greater possibilities for catalyst recovery is by employing a catalyst composition formed in part from a modified phosphorus ligand. In copending U.S. patent application Ser. No. 479,923, filed Feb. 14, 1990, a bidentate phosphorus ligand also containing a hydroxyl group is reacted with a modifier compound, typically an inorganic solid, to produce an immobilized bidentate phosphorus ligand. The nature of the hydroxyl-substituted bidentate ligand is of some importance in how well interaction between the ligand and the modifier compound takes place. The known ligand 1,3-bis(diphenylphosphino)-2-hydroxypropane is useful for the production of immobilized ligands but the hydroxyl group is secondary and somewhat sterically shielded by the diphenylphosphine groups. In *Angew. Chem.*, 100(5), pp. 730-731, the compounds 1,3-bis(diphenylphosphino)-2-hexanol and 1,2-bis(diphenylphosphino)-3-hexanol are disclosed and in *J. Coord. Chem.*, 9(4), pp. 235-244, the compound 1,5-bis(diphenylphosphino)-3-pentanol is disclosed. These bisphosphines have a relatively low activity towards the modifier compound due to steric hindrance and/or the hydroxyl group being secondary rather than primary. It would be of advantage to provide a more active hydroxyl-substituted bidentate phosphorus ligand which will react more efficiently to produce an immobilized bidentate phosphine ligand.

SUMMARY OF THE INVENTION

The present invention relates to a novel class of substituted bidentate phosphorus ligands. More particularly, the invention relates to a class of 2-(ω-hydroxyalkyl)-1,3-bis(diarylphosphino)propane compounds.

DESCRIPTION OF THE INVENTION

The present invention provides a class of hydroxyalkyl-substituted bis(diarylphosphino)propane compounds wherein the hydroxyl group is a primary hydroxyl substituent. Such compounds include the bisphosphine structure found to be useful when the bisphosphine is employed as a ligand in catalyst formation, and also a hydroxyl group which is relatively active by virtue of being primary. The compounds of the invention are particularly useful in the production of immobilized bisphosphine ligands by reaction of the hydroxyl group with an acidic function of a solid material such as silica or silica-alumina. Inclusion of the immobilized ligand in the formation of a catalyst composition, e.g., the catalyst compositions useful in production of linear alternating polymers of carbon monoxide and at least one ethylenically unsaturated hydrocarbon, increases the ease with which the catalyst components can be separated and recovered from a product mixture.

The novel compounds of the invention are 2-(ω-hydroxyakyl)-1,3-bis(diarylphosphino)propane compounds represented by the formula

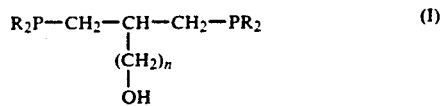

wherein R independently is aryl of up to 10 carbon atoms inclusive and n is a whole number from 2 to 12 inclusive. R is hydrocarbyl containing only atoms of carbon and hydrogen or R is substituted hydrocarbyl containing one or more additional atoms such as divalent oxygen in one or more polar substituents attached to aromatic ring carbon atoms. Such polar groups are preferably alkoxy of 1 to 4 carbon atoms inclusive, and at least one of such groups is attached to an aromatic ring carbon atom which is ortho relative to the carbon atom through which the aromatic ring is attached to the indicated phosphorus. Illustrative of hydrocarbon R groups are phenyl, naphthyl, p-methylphenyl, o-ethylphenyl and 2,4-dimethylphenyl. Illustrative substituted hydrocarbyl groups include 2-methoxyphenyl, 2-methoxy-1-naphthyl, 2,4-diethoxyphenyl and 2-methoxy-4-butoxyphenyl. The preferred R groups are phenyl or 2-methoxyphenyl, particularly the latter group. The hydroxyalkyl substituent of the above formula I is illustrated by 1,2-ethylene, 1,6-hexylene, 1,8-octylene and 1,10-decylene. The preferred hydroxyalkyl groups have from 4 to 8 carbon atoms inclusive.

The preferred hydroxyalkyl bis(diarylphosphino) compounds of the above formula have all R groups the same and are illustrated by 2-(6-hydroxyhexyl)-1,3-bis(-diphenylphosphino)propane, also termed 8-diphenylphosphino-7-(diphenylphosphinomethyl)octan-1-ol, 2-(6-hydroxyhexyl)-1,3-bis[di(2-methoxyphenyl)phosphino]propane, also termed 8-[di(2-methoxyphenyl)-phosphino]-7-[di(2-methoxyphenyl)phosphinomethyl- ]octan-1-ol, and 2-(8-hydroxyoctyl)-1,3-bis[di(2,4-dimethoxyphenyl)phosphino]propane. Particularly preferred are the compounds of the above formula I wherein each R is phenyl or 2-methoxyphenyl and n is 6.

The compounds of the invention are produced by a multi-step synthesis scheme designed to insure that synthetic steps required to introduce one type of substituent onto the ligand molecule do not adversely affect the other substituent groups. A haloalkanol of up to 12 carbon atoms is a particularly useful starting material and in a first process step a haloalkanol of the formula $$HO\text{-}(CH_2)_n\text{-}X \quad \text{(II)}$$

wherein n has the previously stated meaning and X is a middle halogen, i.e., chlorine or bromine, is reacted with a lower α-olefin to produce a corresponding ether. Olefins such as propylene are satisfactory but preferred is isobutylene. The reaction takes place according to known technology in the presence of strong mineral acid and produces the ether of the formula $$R'\text{-}O\text{-}(CH_2)_n\text{-}X \quad \text{(III)}$$

wherein n and X have the previously stated meanings and R' is an alkyl group corresponding to the α-olefin employed in the reaction. For example, the reaction of the haloalkanol of formula II with propylene produces an ether of formula III wherein R' is isopropyl. Alternatively, use of isobutylene produces an ether wherein R is t-butyl. The formation of the ether substituent according to this process step serves to protect the hydroxyl group against undesirable side reactions.

In a second process step, the haloether of the first process step is converted to an alkoxyalkyl dialkyl malonate compound by reaction with dialkyl malonate, e.g., diethyl malonate, in the presence of a strong base such as an alkali metal hydride, e.g., sodium hydride. The resulting product is represented by the following formula when diethyl malonate is the dialkyl malonate reactant

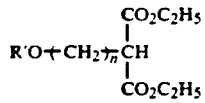

$$\quad \text{(IV)}$$

wherein n and R' have the previously stated meanings.

The third process step comprises the reduction of the diester of formula IV to the corresponding dialcohol as by treatment with a stoichiometric reducing agent such as lithium aluminum hydride in diethyl ether. This conversion is also broadly conventional and produces the diol of the formula

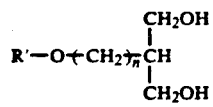

$$\quad \text{(V)}$$

wherein R' and n have the previously stated meanings.

The fourth process step introduces the phosphine functionality by transforming the diol of formula V to the ditosylate or similar derivative followed by reaction with metal diarylphosphide, particularly an alkali metal diarylphosphide. The alkali metal of preference is sodium and the sodium diarylphosphide is conveniently produced in situ by reaction of sodium hydride in dimethyl sulfoxide with a diarylphosphine of the formula $R_2PH$ to produce an alkoxyalkyl bis(diarylphosphino)propane of the formula

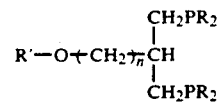

$$\quad \text{(VI)}$$

wherein R, R' and n have the previously stated meanings.

The fifth and final process step is the removal of the protecting R' group to form the hydroxyaryl bis(diarylphosphino)propane compound

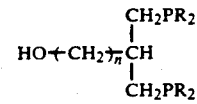

$$\quad \text{(VII)}$$

wherein n and R have the previously stated meanings. This ether cleavage step typically takes place in the presence of a strong aqueous mineral acid such as hydrochloric acid.

Each of the above process steps are broadly conventional and well known and are conducted to give the particular product in good yield. Taken together, the five-step process serves as an efficient method of producing the hydroxyalkyl bis(diarylphosphino)propane compounds of the invention in good yield and with a high product purity.

The hydroxyalkyl bis(diarylphosphino)propane compounds of the invention are useful as bidentate phosphine ligands in the production of catalyst compositions. A particular utility is in the formation of catalysts used to promote the production of linear alternating polymers of carbon monoxide and at least one ethylenically unsaturated hydrocarbon, e.g., copolymers of carbon monoxide and ethylene or terpolymers of carbon monoxide, ethylene and propylene. Such catalyst compositions are typically formed from a compound of palladium such as palladium acetate, the anion of a non-hydrohalogenic acid having a pKa below 2, e.g., the anion of trifluoroacetic acid or p-toluenesulfonic acid, and a bidentate ligand of phosphorus. The hydroxy diphosphine compounds of the invention are suitable for direct inclusion within such catalyst compositions. Preferably, however, the compounds of the invention are used in the production of immobilized ligands which are also referred to as heterogeneous ligands as by reaction of the hydroxyl group present in the molecule with the surface acidity of a solid inorganic compound such as silica. This immobilized ligand is then employed in catalyst compositions as is described in the above copending application Ser. No. 479,923, filed Feb. 14, 1990. The compounds of the invention are particularly important precursors of such immobilized ligands by virtue of a hydroxyl group which is primary and relatively free from steric hindrance. As a result, the interaction to form an immobilized ligand is relatively complete and as a result the opportunity to recover and recycle the bisphosphine ligand is considerably enhanced.

The invention is further illustrated by the following Illustrative Embodiments which should not be regarded as limitations.

ILLUSTRATIVE EMBODIMENT I

The compound 1-t-butoxy-6-chlorohexane was prepared by mixing in a pressure bottle 41.0 g (0.3 mol) of 6-chlorohexanol-1, 300 ml of liquified isobutylene, 300 ml of methylene chloride and 3 ml of 98% sulfuric acid. The bottle and contents were maintained at 20° C. for 16 hours and the contents were then cooled to $-20°$ C. and poured into 250 ml of saturated sodium bicarbonate solution. After unreacted isobutylene was allowed to evaporate, from the two-phase mixture which resulted, the aqueous phase was separated and extracted twice with 50 ml portions of methylene chloride. The extracts were combined and dried over magnesium sulfate. The methylene chloride solvent was removed by distillation, initially at atmoshperic pressure and then at 26.6 mbar. The residue which resulted was then distilled to give 44.9 g (78% yield) of 1-t-butoxy-6-chlorohexane having a boiling point of 42° C.-44° C. at $1.33 \times 10^{-3}$ mbar.

ILLUSTRATIVE EMBODIMENT II

Diethyl 6-t-butoxyheptane-1,1-dicarboxylate was prepared by adding a solution of 27.2 g (0.17 mol) of diethyl malonate in 150 ml of dry dimethylformamide to a stirred, ice-cold suspension of 0.17 mol of sodium hydride in 150 ml of dry dimethylformamide over a period of 0.5 hour. After stirring for an additional 0.5 hour at 20° C., 28.9 g (0.15 mol) of the product of Illustrative Embodiment I and 4.5 g (0.03 mol) of dry sodium iodide were added and the mixture was warmed to 70° C. After 24 hours at 70° C. the resulting mixture was cooled to 20° C. and diluted with 2.5 liters of ice water and then extracted four times with 250 ml portions of diethyl ether. The combined extracts were washed with 50 ml of saturated aqueous sodium bicarbonate, 50 ml of water and 50 ml of brine, and then dried over magnesium sulfate. The solvent was removed by distillation, initially at atmospheric pressure and then at 26.6 mbar. A pale, yellow oil (46.4 g) was obtained which was distilled to give 34.7 g (a 73% yield) of a colorless liquid having a boiling point of 115° C.-118° C. at $9.31 \times 10^{-3}$ mbar. The proton nuclear magnetic resonance spectrum of the compound was consistent with diethyl 6-t-butoxyheptane-1,1-dicarboxylate.

ILLUSTRATIVE EMBODIMENT III

The compound 2-(6-t-butoxyhexyl)propane-1,3-diol ditosylate was prepared by adding in a dropwise manner over 45 minutes a solution of 35.8 g (113.3 mmol) of the product of Illustrative Embodiment II in 140 ml of dry diethyl ether to an ice-cooled suspension of 5.84 g (153.7 mmol) of lithium aluminum hydride in 160 ml of dry diethyl ether. After refluxing for 6 hours, the resulting mixture was cooled in ice and cautiously treated with 10 ml of ethyl acetate, with 25 ml of water and then with an aqueous solution of 1 g of sodium hydroxide in 5.5 ml of water. The resulting suspension was mixed with a filter aid and then filtered. The filter cake was extracted by stirring with three 150 ml portions of ethyl acetate and again filtered. The combined organic extracts were dried over magnesium sulfate and concentrated at an initial reduced pressure of 133 mbar and then at 26.6 mbar. A colorless viscous oil (26.3 g, 100% yield) was obtained.

This oil was dissolved in 25 ml of dry pyridine, cooled to 0° C. and added to a stirred solution of 64.8 g (0.34 mol) p-toluenesulfonyl chloride in 125 ml of dry pyridine which was also at 0° C. After the mixture was stirred at 0° C. for 2 hours and at 20° C. for 16 hours, the mixture was diluted with 250 ml of ice water and, after stirring an additional 1 hour was extracted with four 125 ml portions of diethyl ether. The combined extracts were washed with concentrated citric acid until acidic, with 50 ml of water, saturated aqueous sodium bicarbonate solution and then with 50 ml of brine. The resulting solution was dried over magnesium sulfate and then concentrated at a pressure which initially was atmospheric and then was 26.6 mbar. A pale, brown oil (48.8 g) was obtained which crystallized upon addition of petroleum ether. Recrystallization from a 4:1 by volume mixture of petroleum ether and diethyl ether gave 32.3 g (a 53% yield) of 2-(6-t-butoxyhexyl)propane-1,3-diol ditosylate (di-p-toluenesulfonate), melting point 62° C.-64° C. The proton nuclear magnetic resonance spectra of the product were consistent with this structure.

ILLUSTRATIVE EMBODIMENT IV

The compound 1-t-butoxy-8-[di(2-methoxyphenyl)phosphino]-7-[di(2-methoxyphenyl)phosphinomethyl]octane was produced by the following synthetic scheme which was carried out in a nitrogen atmosphere using degassed solvents which had been saturated with nitrogen.

Sodium hydride (57.3 mmol) was added to 69 ml of dry dimethylsulfoxide and the mixture was heated at 70° C. for 0.5 hr. The resulting homogenous solution was cooled to approximately 20° C. and added under nitrogen pressure over 0.5 hour to a stirred solution of 13.75 g (55.9 mmol) of di(2-methoxyphenyl)phosphine in 46 ml of dry dimethylsulfoxide maintained at approximately 20° C. The resulting solution was then stirred for another 15 minutes and the blood red solution was added to 14.85 g (27.5 mmol) of the product of Illustrative Embodiment III in 46 ml of dry dimethylsulfoxide. The reaction mixture was stirred for 0.5 hour and then poured into 1400 ml of 0.5% aqueous sodium bicarbonate solution which was then saturated with sodium chloride. The resulting mixture was extracted with three 250 ml portions of benzene and the combined extracts were washed with three 25 ml portions of water and dried over sodium sulfate. The solution was concentrated initially at 133 mbar and then at 26.6 mbar. An oily residue, 28.2 g, resulted. The residue was purified by liquid chromatography over silica using a 5:95 by volume mixture of ethyl acetate and hexane as eluent. After evaporation of the solvent a colorless glass was obtained, 14.1 g (a 74.5% yield). The proton nuclear magnetic resonance spectrum of this material was consistent with the structure of the desired product.

ILLUSTRATIVE EMBODIMENT V

The compound 8-di(2-methoxyphenyl)phosphino-7-[di(2-methoxyphenyl)phosphinomethyl]octan-1-ol was produced by the following synthetic scheme which was carried out in a nitrogen atmosphere using solvents which had been degassed and saturated with nitrogen. The product of Illustrative Embodiment IV, 14.1 g (20.5 mmol) was dissolved in 141 ml of concentrated hydrochloric acid and stirred for 2 hours at approximately 20° C. The colorless solution which resulted was washed with two 25 ml portions of benzene and evaporated at 1.33 mbar and a temperature equal to or less than 30° C. The oily residue was treated with a 5% solution of aqueous sodium bicarbonate until it had a pH between 6 and 7. A white precipitate formed which was recovered by filtration and washed with water. The filter cake was dried at 1 mbar and 20° C. for 24 hours which produced a colorless amorphous compound, 12.2 g (a 94% yield), melting point 47°–50° C. Thin layer chromatography indicated that the compound was pure and the proton and $^{31}p$ nuclear magnetic resonance spectra were consistent with the structure of the desired compound.

What is claimed is:

1. As novel compounds, 2-(ω-hydroxyalkyl)-1,3-bis(-diarylphosphino)propane compounds.

2. The compounds of claim 1 of the formula

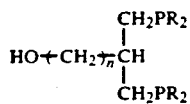

wherein R independently is a nonsubstituted hydrocarbyl aryl of up to 10 carbon atoms inclusive, or a substituted hydrocarbyl aryl of up to 10 carbon atoms inclusive, and n is a whole number from 2 to 12 inclusive.

3. The compound of claim 2 wherein R is a nonsubstituted hydrocarbyl aryl.

4. The compound of claim 2 wherein R is phenyl, with or without substitution, and n is a whole number from 4 to 8 inclusive.

5. The compound of claim 4 wherein n is 6.

6. The compound of claim 2 wherein R is substituted hydrocarbyl aryl, containing at least one polar group as a substituent on a ring carbon atom through which R is attached to the phosphorus.

7. The compound of claim 6 wherein the polar group is alkoxy.

8. The compound of claim 7 wherein n is a whole number from 4 to 8.

9. The compound of claim 8 wherein the polar group is methoxy.

10. The compound of claim 9 wherein each R is 2-methoxyphenyl.

11. The compound of claim 10 wherein n is 6.